United States Patent [19]

Jones

[11] Patent Number: 4,886,075
[45] Date of Patent: Dec. 12, 1989

[54] THERMOELECTRIC ION GENERATOR FOR ENDODONTIC THERAPY

[76] Inventor: J. Paul Jones, 413 N. Saddlebrook Cir., Chester Springs, Pa. 19425

[21] Appl. No.: 279,110

[22] Filed: Dec. 2, 1988

[51] Int. Cl.$^4$ ............................ A61N 1/05; A61N 1/30
[52] U.S. Cl. ................................. 128/787; 128/419 F; 604/20
[58] Field of Search ............... 128/787, 419 F; 604/20

[56] References Cited

U.S. PATENT DOCUMENTS

| | | | |
|---|---|---|---|
| 2,069,112 | 1/1937 | Oppenheim | 128/787 |
| 2,655,922 | 10/1953 | Knappwost | 128/787 |
| 4,027,393 | 6/1977 | Ellis et al. | 604/20 X |

FOREIGN PATENT DOCUMENTS 650630  3/1979  U.S.S.R. ................................. 604/20

Primary Examiner—Lee S. Cohen

[57] ABSTRACT

A thermoelectric anti-bacterial ion generator device, which is needle-like in appearance, and fits into root canals of teeth that are undergoing endodontic therapy. The miniature ion generator focuses a field of positive silver ions on the apex of the tooth root, and on the root membrane; which destroys bacteria in the infected area and enhances the regeneration of new bone and tissue. The generator has a small loop at the top, which enables it to be easily removed after the initial treatment period; or it may remain in the root canal when the tooth cavity is filled, to prevent reoccurrence of infection.

1 Claim, 2 Drawing Sheets

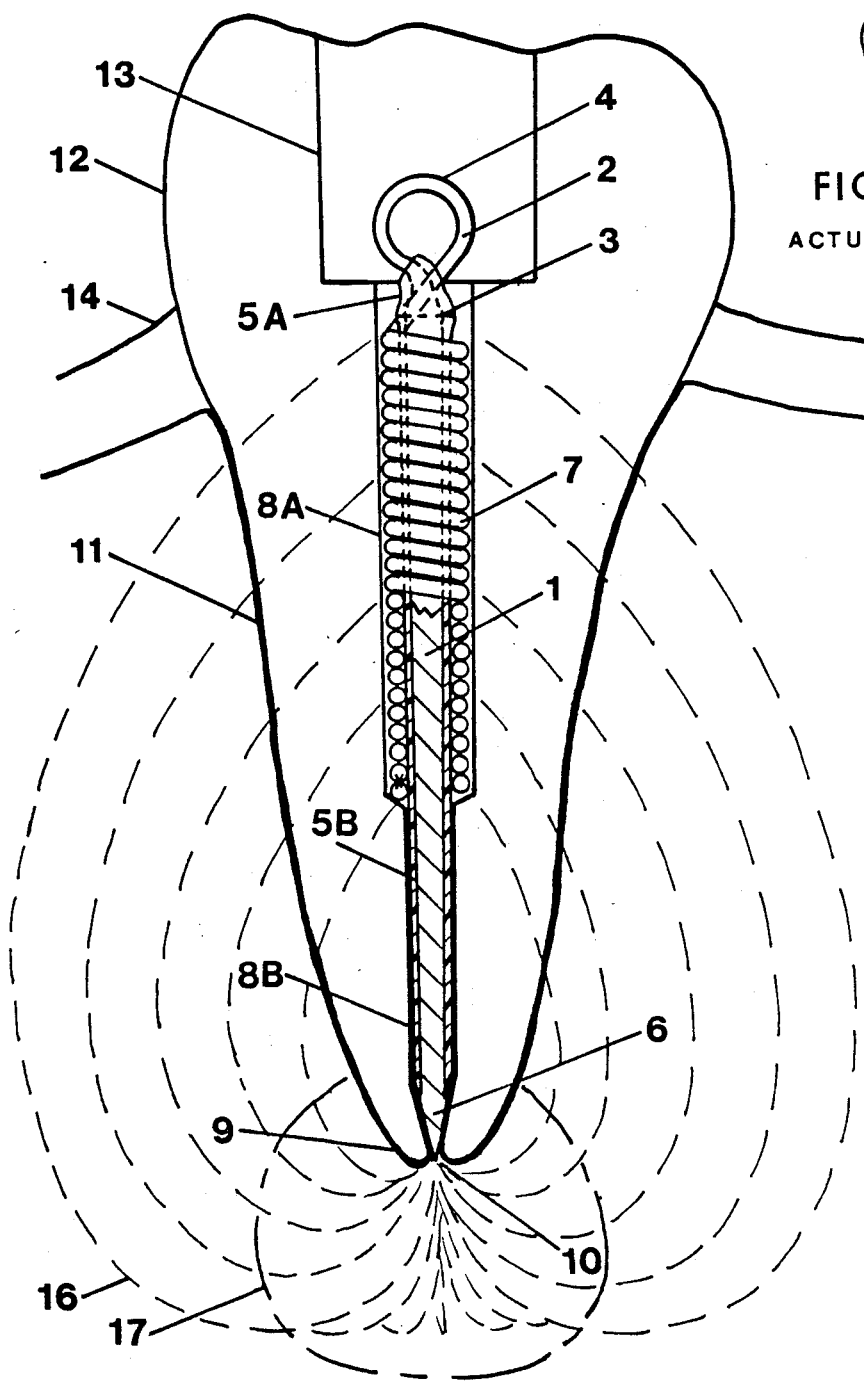
FIG. 1B
ACTUAL SIZE
FIG. 1A

THERMOELECTRIC ION GENERATOR FOR ENDODONTIC THERAPY

This invention provides a means for destroying bacteria that are in an infected bone area around an abscessed tooth. It utilizes metallic ions, which can easily penetrate living bone and tissue, and reach the infected area; which is ordinarily very difficult to reach with antibiotics because of the minimal blood supply. In addition to the antibacterial action of the positive ions, the ion generator provides a positive voltage which stimulates healing and helps the growth and osteogenesis of the degenerated bone.

The needle-like generator is placed in the root canal of a tooth that bas been extirpated during the endodontic therapy process. It is allowed to remain in the root canal during the short healing process, and it would normally be removed before sealing up the crown of the tooth. In severe cases, where there is a chance for reoccurance of the infection at a later date, the ion generator which is made from precious metals, may be sealed into the tooth as a continuing preventative measure, with no adverse affects.

BACKGROUND

Within the dentistry field there is the special area of Endodontics which deals with restoring teeth which have "died" from bacteria that have reached the nerve pulp within the tooth. Most frequently the infecting bacteria have reached the pulp and the nerve of the tooth through cavities in the crown of the tooth. If allowed to go untreated infection will reach the membrane surrounding the root of the tooth, as well as the adjacent bone. If the infection centers around the apex or end of the root, it may become a periapical lesion.

With the best endodontic treatment, a recently abscessed tooth may take many weeks to heal in the bone area. After the dead nerve and pulp of the tooth have been removed and the root canal reamed out by very small hand manipulated reamers. (of the order of 0.005 to 0.040 of an inch diameter) the extirpated root canal may then be plugged and sealed at the crown.

If the pulp infection bas progressed too far to where a lesion can be observed around the apex of the infected root canal, the Dentist may prescribe large doses of antibiotic to help the healing process. However, even when treated with the antibiotic, the lesions may not readily respond and can persist for as long as two years, before completing the healing. This is because so little of the antibiotic can reach the infected area of the bone, because of the very limited blood supply.

When a periapical lesion is allowed to persist for a length of time, such as two years, it frequently developes into a cyst, which is highly infected, and which must be removed by bone surgery, through the gum.

Most dentists that are performing the endodontic therapy will remind the patient of all the variables that can affect the outcome; and that long term infection free use of the tooth cannot be guaranteed.

For all these reasons, there is a need for a superior method of killing bacteria without toxins or antibiotics; because of the affect of antibiotics on the immune system of the body when taken in lengthy doses. Preferably the antibacterial device should be implantable in the tooth, for long term therapy. and prevention of reoccurrence of infection.

As early as 1933, a German dentist named S. Oppenheim placed two dissimilar metal wires, that were soldered together, into the root canal of infected teeth to produce "an electric current"; which had a helpful effect in the healing of the tooth. This is shown in his U.S. Pat. No. 2,009,112. At that time, he was not aware of the more recent developments in Ion Therapy; and he obviously did not have knowledge of the means for shaping an ion field, to guide the ion flow in the desired path; nor did this patent describe or anticipate the many specific requirements for successful endodontic therapy, that are presently used, and which are incorporated in the design of the new ion generator invention.

There are other patents that have been filed which recognize the value of electric current in therapy for diseased teeth and bone.

In 1979 Chlarenza and Weiss U.S. Pat. No. (4,175,565) an electroconductive dental implant that is imbedded in the jawbone of the subject which, with additional external equipment, is used to stimulate osteogenic activity in the bone structure adjacent to the dental implant. Although this patent does not immediately relate to root canal endodontics, it does recognize the use of electric current to increase the rate of normal healing and osteogenic activity.

Also, in 1979 Karostoff and Davidovitch, in their U.S. Pat. No. 4,153,060 , disclosed "apparatus for electrically stimulating bone growth and tooth movement in the mouths of mammals." By incorporating various external electrodes placed on gum surfaces in the mouth, they enhanced the repositioning of specified teeth in conjunction with normal orthopedic practices. In addition to an external constant current power supply and wires into the mouth, the apparatus adds additional cumbersome inhibitions to normal living; that would rule out the continuous or long term use of the system. This is in conflict with the long term continuous tension requirements of the orthopontic process. The system, by admission within the patent, was never used on a human patient.

In 1981 M. J. Nachman patented dental devices for "electrically stimulating a periodontium region within the mouth of a patient." (U.S. Pat No. 4,244,373) His devices are quite cumbersome when added to the mouth of the patient. The devices could not be applied to the patient during his normal course of work, eating etc.; and the patent requires an external power supply and circuitry for operation on a short term basis only.

In 1982 Jeffcoat and Wickham approached the problem of long term implantable bone growth stimulation: by enclosing a battery power supply and associated circuitry within a titanium bullet shaped case, with various external leads, etc., (U.S. Pat. No. 4,333,469) . Although practical for implantation in large difficult bone fractures, by invasive surgery, the approach has no value for treatment within the mouth. The patent does, however, bring out the difficulties in choice of materials, sealents, etc., for long term body implants.

The value of using electric current to enhance and quicken regrowth in bone and body tissue was further revealed in the 1984 U.S. Pat. No. 4,432,361; which describes a "continuously self-monitoring device for expediting the healing of bone or soft tissue fractures or defects." In addition to controlled power supplies, monitor circuits etc., which are external to the patient, the method includes the use of invasive surgery to insert metal electrodes into the flesh and bone ends at a bone fracture site. The method does not anticipate the use of a long term or permanent thermo-electric implant, such as described in the new invention.

SPECIAL PROBLEMS OF ENDODONIIC THERAPY

The formost problem in Endodontic Root Canal Therapy is the difficulty in reaching and curing the infection that invariably follows the death of the nerve in the tooth. The best of antibiotics are relatively ineffective because they cannot be administered into the bone by injection; and antibiotics that are taken orally cannot reach the infected bone in sufficient quantity because of the inadequate blood supply.

Because of these limitations, and the fact that large doses of antibiotics have negative secondary effects it is one object of this invention to project anti-bacterial ions directly to the infected area of the tooth and bone for sustained periods, without unwanted secondary effects.

The field for operating on a tooth is notoriously bad. All kinds of bacteria abound in the mouth and in the surrounding saliva. This calls for a method for killing the bacteria in the infected area; and all the bacteria that could reinfect the area at a later time.

It is, therefore, another object of this invention to provide a sterilizing ion field in and around an infected tooth, to steadily kill both the bacteria that are already present; and new bacteria that may find their way to the infected area via natural routes, or nest in pockets that may be created by the endodontic root canal therapy procedure.

Because prior art systems for applying electrical currents to teeth and bone are generally very cumbersome and are even connected by wires to an external power supply it is a further object of this invention to provide an ion generating insert, which is self contained, with its own thermoelectric current source that provides a continuous ion flow; and which is small enough to readily fit into an extirpated root canal, while using the standard tools and procedures that are presently used for endodontic root canal therapy.

Another incessant problem, which is an unpleasant part of Endodontic Therapy, is the frequent necessity of removing the "final" filling from the canal after it has been, hopefully, sealed for good. Any remaining infection after the reaming out of the canal, treatment, and sealing, can cause pressure and severe pain, which must be relieved if the tooth is to be saved. The removal of filling materials, which may include precious metal points or even metallic reamers is a touchy task, at best; and the process sometimes leads to damage that will cause the lose of the tooth.

It is, therefore still another object of this invention to provide an extremely narrow and flexible (for following the curvature of some canals) thermoelectric element wherein a second metal wire element is wrapped around an insulated first wire element, as a coil, for a minimum of half the length of the unit; and which (1) does not add appreciable stiffening of the whole device, because of its coil form, and which (2) may be "spiraled out" of the cavity from the crown end for easy removal, if it should become necessary.

Most of the prior art systems, as referred to in the background section, apply electric current in maximum doses to general areas of the gum or jaw bone and, as described, are used for clinical treatment.

It is, therefore, an important object of the new root canal ion generator to provide a minimal sized device that requires minimal power, and which doubles as the temporary or permanent filling plug for an extirpated root canal. The generator is also designed to remain in the canal over long periods to slowly restore bone that has degenerated from persistent infection; and to prevent the reoccurrence of infection from any small inadvertent leak in the root canal sealing system.

To make possible a minimal sized thermoelectric powered ion generator system, that will fit into a typical prepared root canal, it is necessary for the generator design to provide a concentrated shaped field, which is directed to the source of the infection. Bone infection is invariably centered at the apex of the root, and, in time, will continue to spread along the membrane between the root and the surrounding bone.

The features of the new self powered ion generator design for providing a shaped ion field, while doubling as the permanent but easily removeable sealing plug in ENDODONIIC root canal therapy, will be more thoroughly described in the following drawings, patent description and appended claims.

FIG. 1A shows a general cross sectional view of a tooth with an ion generator unit installed in a prepared root canal; and the positive ion flow from the tip of the anode at the root apex which continues through the root membrane to the cathode coil of the generator.

FIG. 1B is an actual sized drawing of the same tooth and ion generator insert, to demonstrate the minuscule dimensions of the device.

OPERATION OF THE SYSTEM

Figure 2:
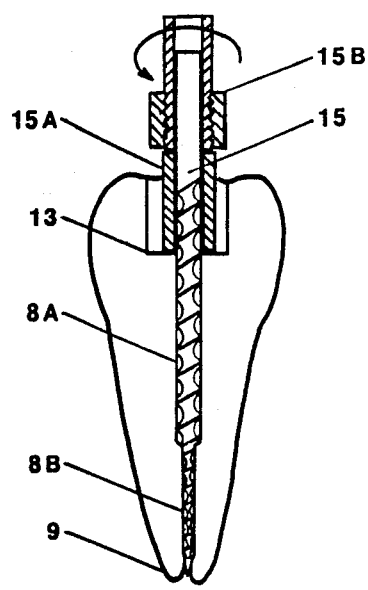
FIG. 2 shows a tooth being prepared with a special, two level reamer, with an adjustable stop handle.

It is important to point out that installation of the new root canal ion generator only requires conventional techniques and tools, that are presently being used by the Endodontic Dentists.

The root canal of the tooth, which normally contains the live nerve of the tooth, is extremely small in dimension—starting at around 0.005 to 0.015 inches wide at the root canal aperture 10, and tapering up to as such as 0.040 inches wide at the top of the canal. These are extremely small dimensions—especially near the root apex—and very fine tapered files and reamers are required to slowly clean out and ream the canal up to the desired size.

The endodontic micro files and reamers are available in sets of seventeen slowly increasing sizes, from four thousandths of an inch to around forty thousandths. This fine gradation of sizes is necessary to allow the Endodontist to clean out and ream the root canal in very small increasing steps; because the smallest sizes are virtually the size of a pair and susceptible to breaking off in the canal when over stressed.

FIG. 1A shows a root canal ion generator unit that is installed in a prepared root canal 8A,8B of a tooth which has been finish reamed with a special two level reamer to diameters 8A and 8B to the exact size of the ion generator insert.

For clarity, the ion generator has been considerably wider (approximately twice oversize), than it would be if shown to exact scale. Also, the actual root canals of the teeth are often curved; especially near the end of the root. This is one of the reasons that the cathode wire 2 is coiled around the center anode pin 1 and its insulating sleeve 5A 5B. since the coil 7 is free to bend with a curved canal 8A,88 without adding appreciable stiffness to the total assembly. A second design reason for the coiling of the cathode wire 2 is to allow it to be easily "spiralled out" of the cemented root canal 8A, if it should become necessary.

The important feature of easy removal will be described more fully later with the aid of FIGS. 4 and 5.

With reference to FIG. 1A fabrication of the minuscule ion generator begins with folding a medical grade insulating plastic (such as Dupont Teflon) sleeve 5B on the tapered anode pin 1, of a first metal such as Silver, after it has been welded to a second metal cathode wire 2, such as platinum. The weld forms a thermocouple junction 3 at the upper end of the silver anode pin 1, which is also covered by the insulating sleeve 5A. The insulating sleeve 5A,5B is continuous down to the anode point 6, at the aperture 10 of the root canal, which is at the apex 9 of the root.

The cathode wire 2 after being formed into a cathode pull loop 4, is wound around the insulated anode pin 1 down to approximately 5 mm from the tip of the anode pin 6, and welded to itself at the last turn of the cathode coil 7. It will be shown that the placement of the cathode coil 7 over the upper section of the insulated and pointed anode pin 1 provides the shaping of the positive ion field 1B around the apex 9 and membrane 11 of the root of the tooth.

The point of the anode pin 6 which emerges from the insulating sleeve 5B at the root canal aperture 10, acts to promote the emission and concentration of positive silver ions 16 at the apex 9 of the root, where the bone infections from the root canal are invariably centered. This first centering of the infection at the root apex is most commonly called an abscess or periapical lesion 17.

If allowed to progress the infection will move from the apex concentration up along the membrane 11 of the tooth root, with a resultant deteriation of the adjacent bone; and, thereafter, observable drainage along the gum line 14.

It is, therefore, a major objective of the ion field 16 shaping to focus and distribute the positive ion flow into the pattern most desirable to reach the most typical geometry of the root infections. The ion flow pattern 16 is depicted in FIG. 1A as the dotted flow lines., which are emitted in a stream from the pointed tip B of the anode pin 1 and then begin to diverge because of the mutual repulsion of the like through the membrane 11 around the periphery of the root as they are attracted by the opposite polarity cathode coil 7.

The curved diverging and oonverging ion paths are both calculable and observable, because of the opposing forces of (1) the mutual repulsion of the positive ions and (2) the attraction force of the negative cathode coil area. The resultant equipotential paths of the ions as shown are almost intuitive.

INSTALLATION FEATURES

Next to the prime objective of creating an anti-bacterial device, which can replace antibiotics in treating hard to reach infected bone areas, while also promoting the growth of deteriorated bone, the most important requirement for the success of this new dental product is the ease with which it can be integrated into the well established system.

in the special field of Endodontios, the Dentists are well trained in the art of treating diseased root canals of teeth and adjacent bone. It takes both special skills and experience to carry out the tooth and bone saving process after tooth death and associated infection. Some of the technical difficulties, such as the extreme fineness of the tools required, have already been mentioned. In addition the Endodontist is working against the limitations of X ray photographs to show fine details; and they are working under the constraints of possible tooth lose from accidentally drilling through the end of the root canal, or perforating the side of a root canal.

FIG. 2 shows the final one-step realing operation for preparing a root canal that has already been cleaned out up to a #30 (0.012 inch) sized taper reamer by conventional means. A double width spiral reamer 15 is made part of the installation kit for the ion generator unit. The adjustable test handle 15B is calibrated to the length of the prepared root canal, to provide the perfect final dimensions for the ion generator insert. A set of variable length stop sleeves 15A make the use of the X ray measurement between the bottom of the excavation cavity is and the root apex 9 usable as a more accurate calibration dimension, than it would be from the less discernable crown 2.

Figure 3:
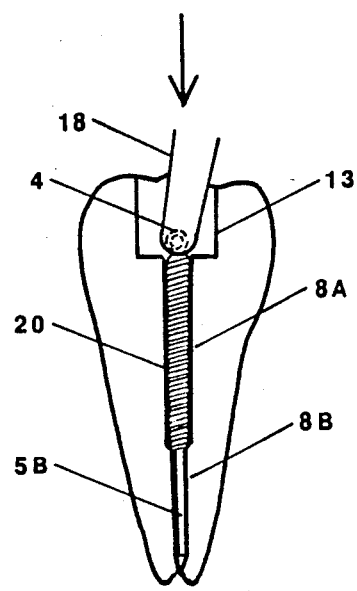
FIG. 3 shows the same tooth of FIG. 2 with the ion generator unit cemented in place, before filling the excavation cavity in the crown.

FIG. 3 shows the insertion and cementing of the ion generator unit into the fully prepared root canal by (1) grasping the cathode pull loop 4 on the generator with dental forceps 18, 12) dipping the generator unit for a initial coating of sealing cement 20 and (3) inserting the unit into the prepared cavity 8A,88. The sealing of the smaller 88 section, which is commonly called the "apical third" is greatly facilitated by the plastic insulating sleeve 6B; which has cold flow characteristics that help fill any slightly out of round sections of the prepared canal section 0B, and the sleeve 5B adds a compression seal at the tapered end 6 of the anode pin 1.

part of the uncertainty that exists in the endodontic treatments is the fluctuation and reoccurance of infection with accompanying pressure and pain which frequently requires the filled root canal to be reopened to relieve the pressure. Temporary fillings are frequently used for observation over many weeks. However, difficulties of removal are increased when "permanent" fillings must be removed for additional treatment.

Figure 4:
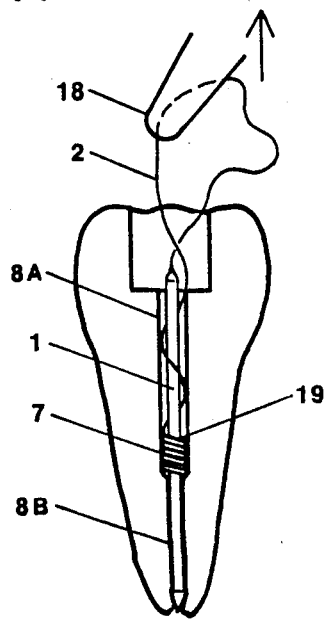
FIG. 4 shows the first step in the easy removal process, which involves the removal of the cavity seal and the "spiralling out" of the coiled cathode wire.

One of the special features of the ion generator design is the easy removal of the cathode wire coil 7, even after it has been cemented in place in the root canal 8A, with reference to FIG. 4 , the cathode wire pull-loop 4 may be grasped with a pair of denial forceps 18 and, when pulled upward, the cathode wire 2 will "spiral out" of the upper cavity 8A, while easily breaking away the small amount of cement 19 associated with each individual turn of the cathode coil 7 .

Figure 5:
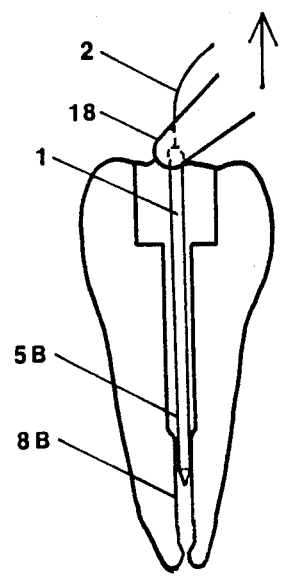
FIG. 5 shows the removal of the anode pin after the cathode wire has been removed; which is easy because of the lubrous insulating coating that had formed a compression seal in the short root apex section.

As shown in FIG. 5 the remaining anode pin 1 which is covered with plastic insulation 5B, is then free to be withdrawn from the relatively short "apical third" of the root canal BB - aided by the lubrous quality of the insulating sleeve 6B The double width reamer 15 would be retained with its final setting to make any secondary cleaning of the canal quick and easy , without risk of root lip penetration.

SUMMATION

It should be clear from the above description that the new Root Canal Ion Generator Insert is a solid advance in the field of Endodontios by providing a heretofore unavailable means to apply antibacterial and bone restoring positive ions to the infected bone around the roots of abscessed teeth. wbile also solving other treatment problems, such as easy filling removal, in the established field of Endodontic Root Canal Therapy.

I claim:

1. An antibacterial and bone restoring ion generating device for implanting in extirpated root canals of teeth during endodontic therapy comprising:
   a pointed center pin of a first metal, which is welded to a second metal wire located at the end of the pin opposite said pointed end, to form a thermo-electro junction;
   a thin coating of insulating material: covering the entire length of said first metal pin except said pointed end and, including the welded junction to said second metal wire;
   a small loop formed from the second metal wire directly adjacent to the insulated thermo-electric junction to act as a handling and pulling convenience;
   a tightly wound coil formed from said second metal wire around said insulated first metal pin. and extending from said loop essentially half way to the pointed end of said first metal pin; said coil forming the cathode of the thermo-electric unit, while allowing easy bending and removal from said root canal; and
   the pointed end of the first metal pin being ground to an essentially 70 degree included angle tapered point, which is the only part of the first metal pin which is not insulated by said coating of insulating material.

* * * * *